United States Patent [19]

Kortright et al.

[11] Patent Number: 4,865,971
[45] Date of Patent: Sep. 12, 1989

[54] MONOCLONAL ANTIBODY SPECIFIC TO A COMMON DETERMINANT SITE OF NEUTROPHILS AND EOSINOPHILS

[75] Inventors: Kenneth H. Kortright, Cooper City; David E. Hofheinz, Homestead; Gary P. Toedter, Miramar, all of Fla.

[73] Assignee: Coulter Corporation, Hialeah, Fla.

[21] Appl. No.: 142,936

[22] Filed: Jan. 12, 1988

Related U.S. Application Data

[63] Continuation-in-part of Ser. No. 68,618, Jun. 30, 1987, abandoned.

[51] Int. Cl.$^4$ .............................................. C07K 15/14
[52] U.S. Cl. .......................................... 435/7; 435/68; 435/172.2; 435/240.27; 435/948; 530/387; 530/809; 935/104
[58] Field of Search ............. 435/7, 68, 172.2, 240.27, 435/948; 530/387, 808, 809; 935/104; 436/548

[56] References Cited

PUBLICATIONS

Lopez et al., *British Journal of Hematology*, 57, 489–494, 1984.
Lopez et al., *Journ. Immunol.*, 134, 3969–3977, 1985.

*Primary Examiner*—Robert J. Warden
*Assistant Examiner*—David A. Saunders
*Attorney, Agent, or Firm*—Myron C. Cass

[57] ABSTRACT

A hybrid cell line capable of producing monoclonal antibodies uniquely specific to human neutrophils and eosinophils and exhibiting no specificity for lymphocytes, basophils and monocytes. Further there is no-reactivity with acute leukemia cells. One of the partners in the hybridoma fusion of a mouse spleen cell developed from using human granulocytes as the immunization agent. The monoclonal antibody further is capable of being used to enumerate and isolate neutrophils in normal peripheral blood and possibly in blood of patients with acute leukemia.

7 Claims, No Drawings

MONOCLONAL ANTIBODY SPECIFIC TO A COMMON DETERMINANT SITE OF NEUTROPHILS AND EOSINOPHILS

RELATED APPLICATION

This application is a continuation-in-part of U.S. Ser. No. 068,618 filed June 30, 1987, and entitled MONOCLONAL ANTIBODY SPECIFIC TO A COMMON DETERMINANT SITE OF NEUTROPHILS AND EOSINOPHILS, now abandoned.

This invention relates to a hybridoma cell line which produces a monoclonal antibody which binds to both the neutrophil and eosinophil populations of leukocytes. The invention thereby enables selective depletion of neutrophils and eosinophils from a peripheral blood sample in a single procedure whereby significant clinically relevant data can be derived as to the remaining leukocyte populations of lymphocytes, basophils and monocytes by other techniques. Also, the selectively depleted neutrophils and eosinophils can be further analyzed.

BACKGROUND OF THE INVENTION

The cellular components of peripheral blood in the circulatory system of a human is comprised principally of red blood cells, i.e., erythrocytes, and white blood cells, i.e., leukocytes. The function of leukocytes and their clinical relevance has generated great interest in the scientific community. The family of leukocytes is comprised of neutrophils, monocytes, eosinophils, basophils and lymphocytes. Many of these cell types have numerous functional subsets.

Neutrophils, monocytes, eosinophils and basophils are known as phagocytes because their primary function in the human immune system is to phagocytose or ingest bacteria and other microorganisms. These cells originate in the bone marrow of a human. However, each of these phagocytes has different functions and behaves as a related but separate system. Although originating in the bone marrow, phagocytic cells do enter into and circulate in peripheral blood.

The general function of the phagocyte system is to achieve phagocytosis by immunological response to a foreign substance. Neutrophils are very efficient as a phagocyte for bacteria that have been coated with an antibody and not as efficient for bacteria without antibody coating. The major function of the neutrophil is to prevent invasion by pathogenic microorganisms by localizing and killing them.

Eosinophils function in the phagocyte system in a manner which is similar to that of neutrophils. In in vitro tests, the two leukocytes may respond to the same antigenic challenges. However, the response of eosinophils generally is not as efficient as neutrophils in terms of phagocytosis and killing bacteria. Recent studies have indicated that eosinophils are important in defense against chronic parasitic infections where neutrophils are not as effective.

The neutrophil is the most common cell in bone marrow and the most common leukocyte in peripheral blood. One microliter of a normal whole blood sample includes, on average, $5 \times 10^3$ leukocytes of which 3,075 are neutrophils, 150 are eosinophils, 25 are basophils, 250 are monocytes and 1500 are lymphocytes. The departure from the normal concentration of neutrophils in peripheral blood has recognized clinical relevance. Thus, increased concentrations of neutrophils, sometimes termed "neutrophilia", may evidence certain disease or physical conditions, while decreased concentrations of neutrophils in peripheral blood, sometimes termed "neutropenia", would have different clinical relevance. In the case of eosinophils, an increase over the normal concentration of eosinophils in a blood sample is termed "eosinophilia"; a decrease in the normal concentration of eosinophils in a blood sample is termed "eosinopenia". Eosinophilia is associated with clinical conditions, such as allergic conditions, drug hypersensitivity reaction and leukemia-like illnesses. Eosinopenia, for instance, is sometimes associated with an ongoing inflammatory process.

Numerous monoclonal antibodies have been developed which bind specifically to neutrophils. Reinherz et al., Leukocyte Typing II: Volume 3, Human Mycloidance Hematopoietic Cells, Springer-Verlag, N.Y., 1986; Girardet et al. American Journal Cancer, Vol. 32, pp 177-183 (1983); Bernstein et al., the Journal of Immunology, Vol. 128, No. 2, pp. 876-881, (February), 1982; Skubitz et al., Blood, Vol 61, No. 1, pp. 19-26, (January), 1983; Majdic et al., Blood, Vol. 58, No. 6, pp. 1127-1133 (December), 1981. The monoclonal antibodies disclosed in these publications exhibit binding specificities for neutrophils, both mature and immature, but have not been shown to bind to a unique determinant site on both neutrophils and eosinophils.

SUMMARY OF THE INVENTION

A cell line which produces a monoclonal antibody to a unique surface protein antigen expressed on both neutrophils and eosinophils circulating in peripheral blood in a human. Attendant advantages from assay applications of such a specific monoclonal antibody are realized.

The monoclonal antibody demonstrates no reactivity with other leukocytes or other human peripheral blood cells. The monoclonal antibody is produced by a hybridoma cell line where one of the partners to the fusion was derived from immunization using human granulocytes.

PREFERRED EMBODIMENT OF THE INVENTION

The monoclonal antibody of the invention is identified by the designation KC-48. It was developed from the fusion of mouse spleen cells immunized with human granulocytes and mouse myeloma cells by standard procedure described by Kohler and Milstein [Nature 256, 495-497 (1975)].

The human granulocytes used were specifically prepared. Blood was obtained by venipuncture from humans and mononuclear cells were separated from granulocytes and red blood cells by Ficoll-Hypaque gradient density sedimentation. Red blood cells and granulocytes then were separated by conventional technique. The granulocytes were collected and any residual erythrocytes were lysed with hypotonic buffer. For immunization, the granulocytes were suspended in phosphate buffered saline (PBS).

$1 \times 10^6$ human granulocytes were injected intraperitoneally into male BALB/C mice three times at two week intervals. Ten days after the third injection, a fourth injection with $5 \times 10^6$ cells was performed. Three days after the fourth injection, the spleen of one mouse was recovered and the spleen cells harvested by conventional techniques and a single cell suspension was made.

The fusion to form hybridomas followed. The spleen cells were washed with mouse myeloma cell line Sp2/0-Ag14 at a ratio of two spleen cells to one myeloma cell in serum free medium. The cells were centrifuged to pellet form and suspended in 40% polyethylene glycol (1500 MW) for eight minutes at 37° C. Then the polyethylene glycol was removed, the cells diluted in HAT media and distributed to microtiter plates.

Cultures were carefully screened after two weeks to identify monoclonal antibodies which reacted with antigens expressed on neutrophils and which did not react with basophils, monocytes, lymphocytes, platelets or erythrocytes. Screening with cytospin preparations eliminated antibodies which did not exhibit the desired specificity detectable within the limits of ultraviolet fluorescent microscopy. Further screening of the cultures employing flow cytometric techniques was successful in identifying the antibodies which bound to antigens expressed only on the surface of granulocytes and in identifying other antibodies which did not exhibit such specific binding capability. Finally, a monoclonal antibody was identified for further characterization because of its strong and apparent selective binding to neutrophils. The monoclonal antibody was identified as producing mouse IgM immunoglobulin by Ouchterlony double diffusion.

The monoclonal antibody embodying the invention is identified as KC-48, although test data associated with this antibody also identifies the monoclonal antibody as CX-7H12-4. Cell surface antigens of granulocytes were labelled by lactoperoxidase iodination. After iodination, the cells were lysed in Non Idet P-40 lysing buffer and the particle-free supernatant was retrieved and cell proteins immunoprecipitated with purified antibody or isotypic control. Protein A conjugated to rabbit anti-mouse IgM was used to precipitate the resulting antigen-antibody complexes. The samples were then subjected to electrophoresis on a 5-15% SDS-PAGE gel, and the radiolabelled proteins detected on X-Ray film. The KC-48 antibody precipitated proteins with molecular weights of 170,000, 135,000 and 99,000 daltons from $^{125}$Iodine labelled granulocyte membranes prepared under reducing conditions. The darkest band was the 99,000 dalton band.

KC-48 was determined to be specific for both neutrophils and eosinophils by flow cytometric analysis of blood cell populations. In one test, the monoclonal antibody was determined to be strongly reactive with granulocytes, showing an average mean channel of 146 on the Epics ® flow cytometer of Coulter Corporation, Hialeah, Fla. Only 10% of the positive cells were brighter than channel 146 on the flow cytometer instrument. Analysis of blood cell populations by gating on relative cell size demonstrated that the KC-48 antibody did not bind platelets, erythrocytes, lymphocytes or monocytes. Gating for monocytes occasionally provided data of a small quantity of monocyte/KC-48 binding, however this was demonstrated to be attributable to the inability of the flow cytometer being able to completely gate out granulocytes from the monocyte area by light-scattering.

Tests were conducted to ascertain other specific binding characteristics of KC-48 antibody. These tests determined that KC-48 will bind also to a myeloid leukemia cell line having neutrophil characteristics, the cell line being identified as HL-60. See Girardet et al. Int. J. Cancer, 32, 177, 1983, supra. The expression of the antigen was very intense, and agglutination of the cells by the KC-48 antibody was very apparent.

Raji (B-cell leukemia), Nalm-1 (null cell leukemia), K-562 (erythrocyte leukemia), HEL (erythrocytic leukemia) and HSB-2 (T-cell leukemia) were tested and determined not to express the antigen recognized by the KC-48 monoclonal antibody.

Further reactivity testing with KC-48 monoclonal antibody was conducted by cell sorting of cells positively stained with the KC-48 antibody employing a flow cytometer instrument. The cells were separated in terms of their relative fluorescent intensity, gated on forward angle light scatter. These tests confirmed the specificity of the KC-48 monoclonal antibody for both neutrophils and eosinophils and that KC-48 did not bind to an antigen expressed on lymphocytes, monocytes and basophils.

A test was conducted which employed magnetic microspheres coated with the KC-48 monoclonal antibody to determine what cell populations would be depleted by this antibody coated entity. The spheres initially were titrated to determine the optimal volume of microspheres for maximum removal of neutrophils without removal of other phagocytic cells, such as, monocytes. This titration was used for further determinations.

TABLE 1

Depletion of Peripheral Blood Populations With Monoclonal Antibody Magnetic Bead Complexes

| Differential Count | Control | KC-48 |
|---|---|---|
| Lymphocyte | 24.8 (5.0)$^a$ | 79.4 (5.7) |
| Monocyte | 7.4 (2.5) | 18.0 (5.5) |
| Neutrophil | 63.7 (5.7) | 0.0 (0.0) |
| Eosinophil | 3.3 (1.2) | 0.0 (0.0) |
| Basophil | 0.7 (0.6) | 2.0 (1.7) |

$^a$ = mean (standard deviation), 500 cells per differential
n = 9

Separate trials were conducted as represented in the tabulated results of TABLE 1. These tabulated results show that the KC-48 antibody coated magnetic beads will deplete neutrophils and eosinophils from a peripheral blood cell population without significant depletion or binding to the other leukocytes. Cells not expressing the KC-48 antigen were enriched in depleted samples by a factor of approximately three times.

A sample of the hybrid cell line capable of producing KC-48 monoclonal antibodies is on deposit with the American Type Culture Collection (A.T.C.C.) and assigned A.T.C.C. No. HB 9584.

The KC-48 monoclonal antibody is unique because of its exceptional specificity for human neutrophils and eosinophils. The antibody expresses no specificity for other human peripheral blood cells. Since the antibody is highly specific for neutrophils and also recognizes the same antigen expressed by eosinophils, detection of granulocytes by any method such as immunofluorescense or immunohistochemistry is greatly facilitated. The monoclonal antibody would be useful in the detection and enumeration of neutrophils and eosinophils in normal whole blood and blood of leukemia patients by flow cytometric techniques. The monoclonal antibody appears to indicate some utility for binding to certain leukemias. The strong expression of the KC-48 antigen on neutrophils and eosinophils enables the antibody to be used effectively in depleting neutrophils and eosinophils from a human peripheral blood population so as to enable the sample of enriched lymphocyte populations to be more precisely enumerated by other procedures. This enrichment of lymphocyte, basophil and monocyte populations is particularly important as applied to basophils. Basophils comprise a very small, difficult to detect cell component of whole blood. By thus withdrawing neutrophils and eosinophils, the enrichment in the remaining sample of basophils from undetected can, in a whole blood sample, be as much 2.1% of the total cells.

Virtually all previously reported monoclonal antibodies reactive with neutrophils do not show reactivity with eosinophils also. T the KC-48 antibody is a unique monoclonal antibody.

We claim:

1. A cell line produced by a hybridoma technique which produces a monoclonal antibody which specifically binds to the KC-48 antigen of neutrophils and eosinophils, and wherein said monoclonal antibody is further characterized as demonstrating no reactivity with other human peripheral blood cells.

2. The cell line according to claim 1 wherein said antibody producing hybridoma cells are derived from mice immunized with human granulocytes.

3. The cell line according to claim 1 wherein said antibody producing hybridoma cells are derived from mouse spleen cells immunized with human granulocytes.

4. A cell line produced by a hybridoma technique having the identifying characteristics of the sample on deposit with the American Type Culture collection, A.T.C.C. No. HB 9584 producing antibody to the KC-48 antigen on neutrophils and eosinophils.

5. A monoclonal antibody which specifically binds to an antigen on the surface of a neutrophil and eosinophil identified as KC-48, said KC-48 monoclonal antibody being further characterized as not having binding specificity with respect to:

A. human acute leukemia cells
B. other human peripheral blood cells and not having significant binding specificity with respect to granulocyte precursors in bone marrow.

6. A monoclonal antibody which recognizes an antigenic determinant on the surface of neutrophils and eosinophils having molecular weights of 170,000, 135,000 and 99,000 daltons as determined by electrophoresis methodology applied to the antigen and comparing the antigen movement with that of known proteins of known molecular weight.

7. A monoclonal antibody produced by a hybridoma cell line having the identifying characteristics of the sample on deposit with the American Type Culture Collection, A.T.T.C.

* * * * *

UNITED STATES PATENT AND TRADEMARK OFFICE
CERTIFICATE OF CORRECTION

PATENT NO. : 4,865,971

DATED : September 12, 1989

INVENTOR(S) : Kenneth H. Kortright, David E. Hofheinz and Gary P. Toedter

It is certified that error appears in the above-identified patent and that said Letters Patent is hereby corrected as shown below:

Column 6, Line 25, after A.T.C.C. insert --No. HB 9584.--

Signed and Sealed this

Seventh Day of January, 1992

Attest:

HARRY F. MANBECK, JR.

Attesting Officer

Commissioner of Patents and Trademarks